United States Patent [19]

Hagen et al.

[11] Patent Number: 5,750,759
[45] Date of Patent: May 12, 1998

[54] CONTINUOUS CATALYTIC PROCESS FOR PREPARATION OF ORGANIC CARBONATES

[75] Inventors: Gary P. Hagen, West Chicago; Michael J. Spangler, Sandwich, both of Ill.

[73] Assignee: Amoco Corporation, Chicago, Ill.

[21] Appl. No.: 834,986

[22] Filed: Apr. 7, 1997

Related U.S. Application Data

[60] Provisional application No. 60/021,375, Jul. 8, 1996.

[51] Int. Cl.⁶ .................................................. C07C 68/00
[52] U.S. Cl. ............................................ 558/277; 502/73
[58] Field of Search .................................................. 558/277

[56] References Cited

U.S. PATENT DOCUMENTS

| | | | |
|---|---|---|---|
| 4,625,044 | 11/1986 | Curnutt | 558/277 |
| 5,004,827 | 4/1991 | Curnutt | 558/277 |
| 5,391,803 | 2/1995 | King et al. | 558/277 |

*Primary Examiner*—Johann Richter
*Assistant Examiner*—Michael G. Ambrose
*Attorney, Agent, or Firm*—Thomas A. Yassen; Frederick S. Jerome; Robert E. Sloat

[57] ABSTRACT

A process of contacting a feedstream containing dioxygen, carbon monoxide, ether, and alkanol, which can be vaporized under conditions of reaction, with a blend of catalysts which are heterogeneous to the feedstream, under conditions of reaction sufficient to form a mixture containing at least one higher molecular weight oxygenated organic compound is described. In another aspect, this invention relates to a blend of catalysts consisting of at least one molecular sieve, natural or synthetic, which has been found useful for hydrocarbon conversion reactions and a catalyst comprising a metal halide or a mixed metal halide supported on active carbon, which is effective in catalyzing direct formation of organic carbonates.

9 Claims, No Drawings

CONTINUOUS CATALYTIC PROCESS FOR PREPARATION OF ORGANIC CARBONATES

CROSS-REFERENCE TO RELATED APPLICATION

This application claims the benefit of U.S. Provisional Application Number 60/021,375, filed Jul. 8, 1996, which application is specifically incorporated herein, in its entirety, by reference.

TECHNICAL FIELD

The present invention relates to a continuous vapor phase process for catalytic production of oxygenated organic compounds, particularly, organic carbonates. More specifically, it relates to contacting a feedstream containing dioxygen, carbon monoxide, ether, and alkanol which can be vaporized under conditions of reaction, with a blend of catalysts which are heterogeneous to the feedstream, under conditions of reaction sufficient to form a mixture containing at least one higher molecular weight oxygenated organic compound.

In another aspect this invention relates to a blend of catalysts consisting of at least one molecular sieve, natural or synthetic, which has been found useful for hydrocarbon conversion reactions and a catalyst comprising a metal halide or a mixed metal halide supported on active carbon which is effective in catalyzing direct formation of organic carbonates.

BACKGROUND OF THE INVENTION

Octane demand has risen in recent years and the growth is likely to continue in the United States. For example, it has been estimated that clear pool octane demand has been increasing by 0.15 units/year in recent years. The addition of alcohols and ethers such as methanol, ethanol and methyl t-butyl ether to gasoline to improve octane number and/or improve the effect of gasoline combustion in internal combustion engines on the environment has been the subject of a number of recent publications.

Methanol is generally made from synthesis gas and ethanol can be made by carbonylation of methanol or more usually from agricultural products by fermentation. Higher alcohols can also result from the catalyzed conversion of synthesis gas. Olefins such as ethylene and propylene are made in large quantities by the cracking of alkanes such as ethane, propane and naphtha. Potentially, additional large amounts of ethylene are available from natural gas by the oxidative coupling of the methane component.

Methanol, while effective if used essentially pure for transportation fuel, is not a good additive for gasoline and is also potentially available in large quantities by the partial oxidation the methane component in natural gas. Ethanol has shown promise as a gasoline additive, but i-butanol in particular is valuable as it can be dehydrated to i-butene and reacted with methanol to form methyl t-butyl ether which is an excellent octane improver that can be easily blended into gasoline. The i-butanol is also an effective octane improver. The methyl ether of i-pentanol is also an excellent octane improver for gasoline. U.K. Patent Application GB 2,123,411 describes a process for making a mixture of octane improving ethers by synthesizing an alcohol mixture containing methanol, ethanol, and higher alcohols and dehydrating the higher alcohols and etherification.

Because of the large amount of methanol available and its problems as a gasoline additive, processes which convert methanol to effective gasoline additives are valuable. Well-known is the Mobil process for converting methanol to gasoline-range hydrocarbons over an aluminum-containing molecular sieve.

In recent years there has been an upsurge in interest in the production of both chemicals and transportation fuels from non-petroleum carbon sources such as methane, tar sands, oil shale and the like. This interest has focused for lack of good direct conversion processes on indirect processes, which often go through a synthesis gas intermediate with subsequent conversion of the synthesis gas via Fischer-Tropsch and related processes to hydrocarbons and/or oxygenates. Oxygenates, particularly lower alcohols, are common products of such synthesis gas reactions, and high conversion, selective processes to convert an alcohol or a mixture of alcohols to higher molecular weight alcohols have substantial commercial potential.

Lower molecular weight oxygenated organic compound, in particular organic carbonates, are useful intermediates in the chemical field, and among these dimethyl carbonate is widely used as an additive for fuels, as an organic solvent and in the synthesis of other carbonates, both alkyl and aryl. Organic carbonates are, also, useful as synthetic lubricants, monomers for organic glass, plasticizers or as reagents in methylation and carbomethoxylation reactions for the preparation of phenol ethers, quaternary salts of ammonium, ureas, urethanes, isocyanates and polycarbonates.

Typical methods for preparation of alkyl carbonates consist in reaction of an alcohol with phosgene, as described for example in Kirk-Othmer, "Encyclopedia of Chemical Technology", 3rd ed., N.4, page 758. This procedure, however, has numerous technical problems (elimination of the hydrochloric acid produced in the reaction), as well as safety problems owing to the use of phosgene.

To overcome these technical problems, alternative methods of synthesis have been proposed, such as the oxidative carbonylation of methanol in the presence of catalysts based on palladium (see, for example, U.S. Pat. No. 4,361,519; German Patent No. 3,212,535 and British Patent No. 2,148,881), based on copper (see, for example, U.S. Pat. No. 3,846,468; U.S. Pat. No. 4,218,391; and U.S. Pat. No. 4,318,862) or based on cobalt (see, for example, Italian Patent Application No. 20809 A/90 and No. 000374 A/91).

These methods of synthesis have, however, some disadvantages owing to the fact that reaction is carried out in a liquid phase and under basically homogeneous catalysis conditions. In the above methods, the reaction system has, in fact, a high sensitivity to the water produced which reduces both the selectivity of carbon monoxide toward formation of dimethyl carbonate, and the rate of reaction. There is difficulty in separating catalyst from reaction products and, when a catalyst based on copper is used, there is high corrosion of the reaction medium.

To overcome these disadvantages, processes carried out in a gas phase have been proposed wherein the organic carbonates are produced starting from methanol, carbon monoxide and dioxygen operating in the presence of an oxidative carbonylation catalyst. Examples of these catalysts are: supported salts and complexes of copper, systems which are generally rapidly deactivated and, in some cases, release hydrochloric acid and form corrosive mixtures (see, for example, U.S. Pat. No. 3,980,690; Italian Patent No. 1,092,951; U.S. Pat. No. 4,625,044; U.S. Pat. No. 5,004,827; and U.S. Pat. No. 4,900,705); supported salts of palladium, systems which combined with nitrogen oxides, nitritoalkanes, dioxygen, carbon monoxide, produce organic carbonates but cause technical problems due to the use of nitritoalkanes and nitrogen oxides (see, for example, European Patent No. 425 197); and supported oxides, salts and complexes of cobalt (see, for example, European Patent Application No. 0 558 128 A2).

In the past various molecular sieve compositions natural and synthetic have been found to be useful for a number of hydrocarbon conversion reactions. Among these are alkylation, aromatization, dehydrogenation and isomerization. Among the sieves which have been used are Type A, X, Y and those of the MFI crystal structure, as shown in "Atlas of Zeolite Structure Types," Second Revised Edition 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-II (Chu, in U.S. Pat. No. 3,709,979), Zeolite ZSM-12 (Rosinski, et al., in U.S. Pat. No. 3,832,449), and others.

Prior are liquid and gas-phase processes for synthesis of organic carbonates, in particular, dimethyl carbonate via Cu(II)-catalyzed oxidative carbonylation of methanol, offer limited reactor performance as the result of the effects of water formed as a co-product. Reactor water inhibits the catalytic reaction and limits reactant conversion to about 30 to 40 percent. In halide-containing fixed bed catalyst systems water leaches halide away from the catalyst resulting in long-term deactivation and excessive corrosion of metallic reactor and downstream hardware components (WO Patent No. 87 07601).

There is, therefore, a present need for catalytic processes to prepare organic carbonates which do not have the above disadvantages. An improved process should, advantageously, be carried out in the vapor phase using a suitable catalyst system which provides improved conversion and yield. Such an improved process which converts lower value compounds to higher value organic carbonates would be particularly advantageous. Dimethyl ether is, for example, less expensive to produce than methanol on a methanol equivalent basis and its oxidative carbonylation to dimethyl carbonate does not produce water as a co-product.

SUMMARY OF THE INVENTION

Economical processes are disclosed for catalytic production of organic carbonates and/or other oxygenated organic compounds. The improved processes of the present invention comprise contacting a feedstream containing dioxygen, carbon monoxide, ether and alkanol which can be vaporized under conditions of reaction, with a blend of catalysts which are heterogeneous to the feedstream, under conditions of reaction sufficient to form a mixture containing at least one higher molecular weight oxygenated organic compound.

In another aspect, the invention is a blend of heterogeneous catalysts for conversions of a feedstream containing dioxygen, carbon monoxide, ether, and alkanol which can be vaporized under conditions of reaction, to form a mixture containing at least one higher molecular weight oxygenated organic compound which blend comprises at least one molecular sieve, and a metal catalyst comprising a metal halide, metal oxide, or metal alkoxide on a suitable support. The metal catalyst component of the blend is, preferably, a metal halide or a mixed metal halide supported on activated carbon.

For a more complete understanding of the present invention, reference should now be made to the embodiments illustrated in greater detail in the accompanying drawing and described below by way of examples of the invention.

BRIEF DESCRIPTION OF THE DRAWING

The accompanying FIGURE is a graphicak depiction of experimental results from a preferred aspect of the present invention for improved production of dimethyl carbonate and other oxygenated organic compounds using the dual catalyst system of the present invention.

GENERAL DESCRIPTION

According to the invention there is provided a catalyst system and process which can economically and efficiently convert a feedstream containing dioxygen, carbon monoxide, ether and alkanol, under conditions of reaction sufficient to form a mixture containing at least one higher molecular weight oxygenated organic compound.

The $C_1$ or higher alkanols useful herein are $C_1$ to $C_{20}$ alkanols such as methanol ethanol, a propanol, a butanol, a pentanol, a hexanol, a nonanol, a dodecanol, and the like. The only limitation on such alcohols is their ability to be vaporized and passed over the catalyst at a temperature low enough to avoid substantial decomposition. Preferred alkanols are one or more members of the group consisting of methanol, ethanol, 1-propanol, 2-propanol, 1-butanol, 2-butanol and 2-methyl-1-propanol. More preferably, it is methanol, ethanol, and mixtures thereof. Most preferably, it is methanol.

The $C_2$ or higher ethers useful herein are $C_2$ to $C_{12}$ ethers symmetrical or asymmetrical. Preferably the ether are one or more members of the group consisting of dimethyl ether, methyl ethyl ether, diethyl ether, methyl n-propyl ether, methyl isopropyl ether, methyl n-butyl ether. More preferably, it is dimethyl ether, diethyl ether, and mixtures thereof. Most preferably, it is dimethyl ether.

Such feeds can also contain one or more $C_1$ to $C_4$ aldehydes or one or more $C_1$ to $C_6$ alkanes and/or alkenes. An especially preferred feedstream is a mixture of methanol, dimethyl ether, dioxygen, nitrogen, hydrogen, carbon monoxide. The feedstream to the process may in addition contain small amounts of one or more of methane, nitrogen, hydrogen, and carbon dioxide.

In general, after the feedstream is passed over the catalyst it will contain a mixture of organic oxygenates at least one of which is of higher molecular weight than any of the starting alkanol or ether. For example, a mixture of methanol and dimethyl ether produces at least dimethyl carbonate, and a mixture of ethanol and dimethyl ether produces at least diethyl carbonate; a mixture of n-propanol and di-n-propyl ether produces at least di-n-propyl carbonate; etc. Generally, small amounts of non-oxygenated products such as methyl chloride also occur in the product. A mixture of methanol and dimethyl ether produces dimethyl carbonate and dimthoxymethane.

Broadly, according to the present invention, there is provided a catalyst system which comprises a blend of (i) at least one molecular sieve, preferably a crystalline metalosilicate exhibiting the MFI crystal structure, and (ii) a catalyst comprising a metal halide or a mixed metal halide, generally on a suitable support, and preferably supported on activated carbon.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Zeolitic materials, both natural and synthetic, useful herein have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform it, size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Manufacture of the ZSM materials utilizes a mixed base system in which sodium aluminate and a silicon containing material are mixed together with sodium hydroxide and an organic base, such as tetrapropylammonium hydroxide and tetrapropylammonium bromide, under specified reaction conditions, to form the crystalline aluminosilicate.

A preferred class of molecular sieves useful, according to the present invention, are crystalline borosilicate molecular sieves disclosed in commonly assigned U.S. Pat. No. 4,268,420, U.S. Pat. No. 4,269,813, U.S. Pat. No. 4,292,457, and U.S. Pat. No. 4,292,458 to Marvin R. Klotz, which are incorporated herein by reference.

Suitable for use according to the present invention are, broadly, crystalline borosilicates which comprises a molecular sieve material having the following compositions in terms of mole ratios of oxides:

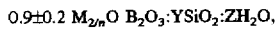

where M is at least one cation having a valence of n, Y is between 4 and about 600, and Z is between 0 and about 160.

Embodiments of such borosilicate provide an X-ray diffraction pattern comprising the following X-ray diffraction lines:

| d (Å) | Assigned Strength |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |

-continued

| d (Å) | Assigned Strength |
| --- | --- |
| 2.97 ± 0.02 | W-M |
| 1.99 ± 0.02 | VW-M | wherein the assigned strengths correspond to the following values of relative peak heights:

| Assigned Strength | Relative Peak Height |
| --- | --- |
| VW | less than 10 |
| W | 10-19 |
| M | 20-39 |
| MS | 40-70 |
| VS | greater than 70 | and "d" represents interplanar spacings, expressed in terms of Angstrom units. A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkyl ammonium cation or a precursor of an alkyl ammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization.

The metal halide component of catalyst blends useful herein is, preferably, a cupric halide. Preferred halogens are one or more members of the group consisting of fluorine, chlorine, bromine, and iodine. More preferably, it is fluorine, chlorine, and mixtures thereof. Most preferably, it is chlorine.

The metal halide catalyst may be used neat, but are advantageously supported on a solid material such as zirconia, titania, boria, alumina, and, particularly, a carbonaceous material such as active carbon and the like, by impregnation or otherwise. Such supports need not be completely inert and, indeed, it appears that the use of active carbon as a support improves certain of the reactions described herein such as that of a mixture of dioxygen, carbon monoxide, methanol and dimethyl ether.

A preferred class of active carbons useful herein are materials disclosed in commonly assigned U.S. Pat. No. 4,082,694 to Arnold N. Wennerberg and Thomas M. O'Grady, which patent is incorporated herein by reference. Such suitable active carbon products are produced from carbonaceous material by a staged temperature process which provides improved yield and processability during manufacture. A source of carbonaceous material, such as crushed coal, coal coke, petroleum coke or a mixture thereof, is heated with agitation in the presence of a substantial weight ratio of hydrous potassium hydroxide at a first lower temperature to dehydrate the combination thereafter the temperature is raised to a second higher temperature to activate the combination which is thereafter cooled and washed to remove inorganic matter and form a high surface area active carbon having a cage-like structure exhibiting micro-porosity, good bulk density and Total Organic Carbon Index.

Active carbon products for use as supports according to this invention have, preferably, an effective surface area greater than about 2,300 square meters per gram and, more preferably, greater than about 2,700 square meters per gram and, most preferably, above about 3,000 square meters per gram as measured by the BET method. Active carbon products for use as supports have, typically, a bulk density greater than about twenty-five hundredths grams per cubic centimeter and, preferably greater than about twenty-seven hundredths grams per cubic centimeter and, more preferably, above about three-tenths gram per cubic centimeter. Further, useful active carbon products preferably have a Total Organic Carbon Index greater than about 300, more preferably, greater than about 500 and, most preferably, greater than about 700.

Blends according to this invention comprise a molecular sieve component and a metal halide catalyst component on a support admixed in proportions of from about 1:19 to about 19:1. Preferred ratios of the molecular sieve component to the supported metal halide component are in a range of from about 1:9 to about 9:1. More preferably, it is in a range of from about 1:5 to about 5:1. Most preferably, it is in a range of from about 1:2 to about 2:1.

Use of a carrier gas mixed with the feedstream to the process can be advantageous. Such materials as carbon dioxide, and inert gases such nitrogen, argon, and the like may be used to improve safety factors including those regarding flammability limits.

According to the present invention, the ratio of alkanol to ether in the feedstreams is any mole ratio which results in the preparation of the desired oxygenated organic compound. Preferably, the ratio of alkanol to ether is between about 10:1 and about 1:10 moles. Preferably, the ratio of alkanol to ether is between about 5:1 and about 1:5 moles. More preferably, the ratio of alkanol to ether is between about 2:1 and about 1:2 moles.

The ratio of dioxygen to total ether and alkanol is, according to the present invention, any mole ratio which results in the preparation of the desired oxygenated organic compound. Preferably, the ratio of dioxygen to total ether and alkanol is between about 1:1 and about 1:1000 moles. More preferably, the ratio of dioxygen to alcohol is between about 1:1 and about 1:100 moles. Most preferably, the ratio of dioxygen to alcohol is between abut 1:1 and about 1:10 moles.

The ratio of dioxygen to carbon monoxide is any ratio which results in the preparation of the dihydrocarbyl carbonates. Preferably according to the present invention, the ratio of dioxygen to carbon monoxide is between about 1:1 and about 1:1000 moles. More preferably, the ratio of dioxygen to carbon monoxide is between about 1:1 and about 1:10 moles.

The dioxygen can be added to the reaction mixture as pure molecular oxygen or diluted with an inert gas such as nitrogen or argon. It is preferred to keep the dioxygen at no more than 10 mole percent of the entire reaction feed so as to avoid the formation of explosive mixtures.

The process can be performed at any temperature and pressure at which the reaction proceeds. Preferred temperatures are between about 20° C. and about 150° C., with between about 90° C. and about 125° C. being more preferred. The most preferred temperatures are between about 115° C. and about 125° C.

The pressure can be atmospheric or super-atmospheric pressure. Preferred pressures are, according to the present invention, between about 1 and about 100 atmospheres, with between about 15 and about 25 atmospheres being most preferred.

The reaction mixture feed gas flow rate, expressed as gas hourly space velocity, can be between about 50 and about 50,000 $hr^{-1}$ and most preferably, between about 100 and about 2,000 $hr^{-1}$. The dihydrocarbyl carbonate can be recovered from the mixture by methods well-known in the art. One particularly desirable method is the use of extractive distillation of the condensed product.

The process of this invention can be performed in either a fixed or fluid bed reactor using either continuous or batch processing methods. It is preferred to use a fixed bed reactor and a continuous mode of operation.

In view of the features and advantages of the continuous vapor phase processes for direct condensation of methanol and dimethyl ether with dioxygen and carbon monoxide feedstream to form a mixture containing at least one higher molecular weight oxygenated organic compound in accordance with this invention as compared to the known methanol condensation systems previously used, the following examples are given.

EXAMPLES

General

Products were analyzed by three gas chromatographic systems. The fixed gases, carbon monoxide and carbon dioxide along with methane were analyzed by an on-line Hewlett-Packard 5730 gas chromatograph equipped with a thermal conductivity detector and a Chromosorb 106 packed column. Analysis was accomplished by using an external standard calibrated for carbon monoxide, carbon dioxide and methane. The non-condensable light gases, $C_1$ to $C_6$, were analyzed off-line using a flame ionization detector and a 6 ft N-octane Porosil C column. The peaks were identified and measured by matching retention times with an external standard containing $C_1$ to $C_6$ hydrocarbons.

The condensable materials were collected in a bomb and analyzed with a flame ionization detector equipped with a 30 m capillary column of fused silica containing RSL 160 liquid phases. Peaks were identified by matching retention times of known alcohols, aldehydes, esters, ketones, olefins and paraffins. Many smaller peaks were not identified. The results are expressed in relative weight percents.

The condensable liquids were also measured on a Hewlett-Packard 5730 gas chromatograph equipped with a thermal conductivity detector. A 6 ft×⅛ in Poropak QS column, 80/100 mesh particles, was used. This system gave semi-quantitative results for water, $C_1$ to $C_6$ alcohols, and some of the lower molecular weight aldehydes, ketones and esters.

In all cases methanol and/or other liquid reactants were metered by use of a syringe pump into a preheat zone of a quartz micro reactor which was electrically heated and operated at atmospheric pressure. Ethylene or nitrogen carrier gas was metered into the top of the down flow reactor by use of Brooks Mass-flow Controllers. Liquid product was collected in a U-tube receiver chilled to −78° C. with a dry-ice isopropyl alcohol cooling bath in most cases or to 0° C. with an ice bath during those cuts when a gas sample was being taken. In all cases, the catalyst volume was 9.4 cc.

Example 1

In this example a new catalytic system was prepared for production of organic carbonates and/or other oxygenated organic compounds from a feedstream containing dioxygen, carbon monoxide, ether and alkanol which can be vaporized under conditions of reaction. This catalytic system was prepared by blending an admixture of (i) crystalline borosilicate molecular sieve in the hydrogen form and (ii)

catalyst containing CuCl$_2$ supported on active carbon. In the resulting blend, the oxidative carbonylation component and the hydrolysis catalyst component are, however, physically separated on separate particles.

Example 2

In this example a blend of catalysts prepared as in Example 1 was tested with feedstreams consisting of dimethyl ether (DME), methanol (MeOH), carbon monoxide (CO) and dioxygen (O$_2$). Productive results were obtained with this blend of catalysts from feedstream consisting of dimethylether, methanol, carbon monoxide, and dioxygen (1/1.1/7.2/1.2 mole ratio). Throughout a 1100 minute test, carried out at 126° C., conversion of dimethylether was steady at from 30 to 33 percent. Methanol conversion was negative, at minus 20 percent to minus 30 percent, which negative result indicated net production of methanol via hydrolysis of dimethylether. Two principle products, dimethyl carbonate (DMC) and dimethoxymethane (DMM), were formed, each in about 50 percent selectivity. Methyl formate and methyl chloride were, also, observed in trace quantities.

This example demonstrated a process according to the present invention which provides net conversion of dimethylether to dimethyl carbonate in an oxidative carbonylation reaction. More specifically, these data demonstrated that water co-produced in the oxidative carbonylation of methanol was consumed in the hydrolysis of dimethyl ether, thus producing a net conversion of dimethylether to dimethyl carbonate which may be summarized by the following simple chemical reactions:

2CH$_3$OH+CO+½O$_2$→CH$_3$O(CO)OCH$_3$+H$_2$O

CH$_3$OCH$_3$+H$_2$O→2CH$_3$OH

Based upon the experimental results net conversion of total methoxy functionality in the feedstream was calculated to take into account the negative conversion (or production) of methanol. Values of this net conversion ranged from 10 to 16 percent during testing in this example.

The apparent formation of dimethoxymethane in this example was unexpected. Dimethoxymethane is the dimethyl acetyl of formaldehyde and its formation may indicate that some of methanol undergoes oxidative dehydrogenation to formaldehyde which then reacts with more methanol to form dimethoxymethane. Where acidic molecular sieves are useful catalysts for acetyl formation, this reaction could be heavily favored in a low-water level reaction environment. (High levels of water could decompose the DMM to methanol and formaldehyde.) Apparent formation of formaldehyde in this system is in contrast to reported accounts of dimethyl carbonate synthesis from methanol/carbon monoxide/dioxygen in which formaldehyde co-production is rarely mentioned. It should be noted that aqueous formaldehyde is difficult to detect via GC analysis and its existence in product mixtures may have gone undetected and unreported in many of these accounts.

Example 3

A blend catalytic system was prepared as in Example 1 except that the active carbon support consisted of a bimodal pore structure described herein above. This blend was tested for oxidative carbonylation of dimethylether and methanol as in Example 2, with a feedstream consisting of dimethylether, methanol, carbon monoxide, and dioxygen (1/1.1/6.7/1.3 mole ratio), but at slightly lower space velocity. Results are presented the Table I below, and in the attached FIGURE.

Example 4

In this example a blend catalytic system, prepared as in Example 1, was tested with feedstreams which consisted of dimethylether/carbon monoxide/dioxygen and 2 percent or 4 percent water under oxidative carbonylation conditions as in Example 2. The blend catalytic system was very effective for hydrolysis of dimethylether to methanol, affording up to 60 percent dimethylether conversions with about 95 percent selectivity to methanol. Conversions of carbon monoxide were about 30 percent, mostly to carbon dioxide.

TABLE I

Dimethyl Carbonate via Oxidative Carbonylation of Dimethylether and Methanol

| Run Time (min) | 120 | 420 | 660 | 900 |
| --- | --- | --- | --- | --- |
| Pressure (psig) | 250 | 250 | 250 | 250 |
| Temp. (°C.) | 95 | 123 | 123 | 122 |
| MeOH conv1, | 75.4 | 37.6 | 47.0 | 40.1 |
| DME conv1, % | 39.4 | 50.3 | 49.1 | 42.0 |
| O$_2$ conv, % | 10.3 | 19.1 | 17.1 | 15.1 |
| CO conv1, % | 5.43 | 7.95 | 7.16 | 5.55 |
| CO conv2, % | 15.9 | 62.4 | 58.1 | 70.9 |
| net MeOH conv Selecivity, % | 51.4 | 46.1 | 48.4 | 41.3 |
| DMC sel (Cl) | 56.0 | 78.8 | 76.2 | 76.9 |
| DMC sel (CO) | 11.6 | 44.2 | 37.1 | 39.4 |
| MeF sel (Cl) | 0 | 1.24 | 1.16 | 1.17 |
| MeF sel (CO) | 0 | 1.39 | 1.13 | 1.20 |
| DMM sel (Cl) | 30.9 | 18.9 | 21.5 | 20.8 |
| MeCl sel (Cl) | 13.2 | 1.08 | 1.13 | 1.09 |
| CO$_2$ sel (CO) | 88.4 | 54.4 | 61.8 | 59.4 |
| DMC Rate (lb/scf/hr) | 0.0662 | 1.39 | 0.988 | 0.960 |

Example 5

In this example a blend catalytic system, prepared as in Example 1, was tested with feedstreams consisting of methanol, carbon monoxide and dioxygen. The blend exhibited good activity and selectivity for the synthesis of dimethyl carbonate.

At conditions of 135° C. and 250 psig, methanol conversion of 30 percent was observed with over 80 percent selectivity to dimethyl carbonate.

Comparative Example A

The oxidative carbonylation reactor was charged with 12.0 cc of catalyst consisting of 7 percent CuCl$_2$ on Darco active carbon supported between plugs of granular silicon carbide. A gas mixture consisting of 98 percent carbon monoxide and 2 percent methane as internal standard was passed through the reactor at a rate of 112.4 sccm. Another gas mixture consisting of 90 percent dioxygen and 10 percent nitrogen was passed through the reactor at a rate of 20.2 sccm. Dimethylether was pumped into the vaporizer preceding the reactor at a rate of 0.04 mL/min. The reactor was maintained at a catalyst bed temperature of 127° C. and a pressure of 150 psig. No organic products were detected in the product stream.

Comparative Example B

A catalyst was prepared consisting of 4.3 percent CuCl$_2$ supported directly on a molecular sieve (hydrogen-exchanged pentasil high-silica zeolite-supported 20 percent on 80 percent gamma alumina) by incipient wetness impregnation of material with a methanolic solution of CuCl$_2$. This wet catalyst was air dried and allowed to dry for several days in a vacuum oven at a temperature of 105° C. The resulting catalyst was tested in a similar procedure to that described above for the oxidative carbonylation of dimethylether. No organic products were observed and some carbon dioxide was detected in the gas stream. At a variety of temperatures ranging from 82° to 250° C. and reactor pressure of 250 psig were tested. The product stream was analyzed at each temperature. Partial dioxygen conversion and carbon monoxide conversion to carbon dioxide was observed at lower temperatures. At the highest temperature of 250° C., dioxygen conversion was complete, and high levels of carbon dioxide were observed in the product stream. Significant levels of methanol were also detected along with lower levels of methyl chloride.

Comparative Example C

A catalyst consisting of cupric chloride supported on a crystalline borosilicate molecular sieve on gamma alumina was tested over a range of reaction temperatures from 110° C. to 273° C. This catalyst did not produce any dimethyl carbonate. At lower temperatures a small amount of carbon dioxide was observed with low reactant conversions. At higher temperatures dioxygen conversion and carbon monoxide conversion were 100 percent with high levels of carbon dioxide formed as the major product. Some methanol was present in the product formed by hydrolysis of dimethylether with water which was, likely, generated by oxidation of dimethylether to carbon dioxide and water. A small amount of methyl chloride was also detected in the effluent.

Comparative Example D

A catalyst consisting of $CuCl_2$ supported on Darco active carbon which contained 7.1 percent copper was tested at a low GHSV of 388 hr−1, the same space velocity as Example 2, and at reaction temperatures from about 100° C. to about 120° C.

While selectivity to dimethyl carbonate reached up to about 80 percent earlier, it decreased to 30 percent and below after 900 minutes. Average net conversion of $CH_3O$ up to 900 minutes was only 43.9 percent. Results are presented the Table II.

TABLE II

| Dimethyl Carbonate via Oxidative Carbonylation of Dimethylether and Methanol | | | | |
|---|---|---|---|---|
| Run Time (min) | 120 | 480 | 660 | 900 |
| Pressure (psig) | 250 | 250 | 250 | 250 |
| Temp. (°C.) | 98 | 119 | 119 | 121 |
| MeOH conv1, % | 95.4 | 39.6 | 62.0 | 67.7 |
| DME conv1, % | 26.4 | 50.5 | 47.6 | 12.1 |
| $O_2$ conv, % | 14.0 | 14.2 | 14.0 | 15.0 |
| CO conv1, % | 4.15 | 6.95 | 7.05 | 7.37 |
| CO conv2, % | 21.4 | 63.6 | 32.3 | 52.0 |
| net MeOH conv | 49.2 | 46.9 | 52.4 | 30.6 |
| Selecivity, % | | | | |
| DMC sel (Cl) | 36.4 | 84.8 | 62.3 | 67.7 |
| DMC sel (CO) | 7.7 | 58.6 | 17.3 | 50.1 |
| MeF sel (Cl) | 0 | 0.35 | 1.42 | 1.55 |
| MeF sel (CO) | 0 | 0.49 | 0.79 | 2.29 |
| DMM sel (Cl) | 45.3 | 13.6 | 31.2 | 29.4 |
| MeCl sel (Cl) | 18.2 | 1.24 | 5.08 | 1.32 |
| $CO_2$ sel (CO) | 92.3 | 41.0 | 81.9 | 47.6 |
| DMC Rate (lb/scf/hr) | 0.0432 | 1.54 | 0.242 | 1.123 |

Comparative Example E

In this example a blend of catalysts prepared as in Example 1 was tested with feedstreams consisting of methanol (MeOH), carbon monoxide (CO) and dioxygen ($O_2$). Productive results were obtained with this blend of catalysts from feedstream consisting of methanol, carbon monoxide, and dioxygen throughout a 1080 minute test, carried out at temperature of 120° C. and pressure of 250 psig. Methanol conversion was 30 percent, and selectivity to DMC was over 80 percent. Results are presented the Table III.

TABLE III

| Dimethyl Carbonate via Oxidative Carbonylation of Methanol Using an Admixture of Crystalline Borosilicate Molecular Sieve and $CuCl_2$ Supported on Active Carbon | | | | |
|---|---|---|---|---|
| Run Time (min) | 180 | 480 | 660 | 960 |
| Pressure (psig) | 250 | 250 | 250 | 250 |
| Temp. (°C.) | 120 | 120 | 120 | 120 |
| MeOH conv1, % | 43.2 | 29.9 | 26.4 | 31.6 |
| DMC prod. | 6.68 | 3.83 | 2.43 | 1.23 |
| $O_2$ conv, % | 26.5 | 14.2 | 9.66 | 9.46 |
| CO conv1, % | 8.70 | 5.29 | 5.93 | 5.06 |
| CO conv2, % | 35.5 | 34.0 | 20.3 | 15.3 |
| Selecivity, % | | | | |
| DMC sel (MeOH) | 78.5 | 78.7 | 68.8 | 62.2 |
| DMC sel (CO) | 82.9 | 81.7 | 77.3 | 60.5 |

That which is claimed is:

1. A processes for catalytic production of organic carbonates which process comprises contacting a feedstream containing dioxygen, carbon monoxide, ether, and alkanol which can be vaporized under conditions of reaction, with a blend of catalysts, which are heterogeneous to the feedstream, under conditions of reaction sufficient to form a mixture containing at least one higher molecular weight organic carbonate.

2. The process according to claim 1 wherein the blend of catalysts comprises at least one molecular sieve and a catalyst comprising a metal halide or a mixed metal halide supported on activated carbon.

3. The process according to claim 2 wherein the molecular sieve is crystalline aluminosilicate exhibiting the MFI crystal structure, and has a silicon-to-aluminum atomic ratio of at least 600.

4. The process according to claim 2 wherein the molecular sieve is crystalline borosilicate exhibiting the MFI crystal structure and has the following composition in terms of mole ratio of oxides:

$$0.9 \pm 0.2 \ M_{2/n}O:B_2O_3:YSiO_2:ZH_2O,$$

wherein M is at least one cation having a valence of n, Y is between 4 and about 600, and Z is between 0 and about 160.0.

5. The process according to claim 2 wherein the molecular sieve is crystalline metalosilicate exhibiting the MFI crystal structure, and the metal halide is cupric halide.

6. The process according to claim 5 wherein the active carbon has an effective surface area greater than about 2,300 square meters per gram as measured by the BET method.

7. The process according to claim 5 wherein the cupric halide is cupric chloride.

8. The process according to claim 1 wherein the ether is one or more members of the group consisting of dimethyl ether, methyl ethyl ether, diethyl ether, methyl n-propyl ether, methyl isopropyl ether, and methyl n-butyl ether.

9. The process according to claim 1 wherein the alkanol is one or more members of the group consisting of methanol, ethanol, 1-propanol, 2-propanol, 1-butanol, 2-butanol and 2-methyl-1-propanol.

* * * * *

UNITED STATES PATENT AND TRADEMARK OFFICE
CERTIFICATE OF CORRECTION

PATENT NO.: 5,750,759
DATED: May 12, 1998
INVENTOR(S): Gary P. Hagen, Michael J. Spangler It is certified that error appears in the above-identified patent and that said Letters Patent is hereby corrected as shown below:

| Col. | Line | |
|---|---|---|
| 5 | 51 | reads "$0.9 \pm 0.2\ M_{2/n}\ O\ B_2O_3:YSiO_2:ZH_2O$" should read --$0.9 \pm 0.2\ M_{2/n}\ O:B_2O_3:YSiO_2:ZH_2O$-- |
| 12 | 22 | reads "A processes for catalytic production" should read --A process for catalytic production heterogeneous-- |
| 12 | 36 | reads "the MFI crystal structure, and has a silico should read --the MFI crystal structure and has a silicon-- |

Signed and Sealed this

Twenty-sixth Day of January, 1999

Attest:

Attesting Officer

Acting Commissioner of Patents and Trademarks